United States Patent
Atkin et al.

(10) Patent No.: US 7,044,736 B2
(45) Date of Patent: May 16, 2006

(54) ULTRASONIC DENTAL INSERT HAVING A HAND GRIP FITTED TO A RETAINING RING

(75) Inventors: Benjamin Atkin, Miami, FL (US); Haim Levy, Hod Hasharon (IL)

(73) Assignee: Discus Dental Impressions, Inc., Culver City, CA (US)

( * ) Notice: Subject to any disclaimer, the term of this patent is extended or adjusted under 35 U.S.C. 154(b) by 0 days.

(21) Appl. No.: 10/734,517

(22) Filed: Dec. 12, 2003

(65) Prior Publication Data

US 2004/0126736 A1 Jul. 1, 2004

Related U.S. Application Data

(60) Provisional application No. 60/432,653, filed on Dec. 12, 2002.

(51) Int. Cl.
*A61C 1/07* (2006.01)
(52) U.S. Cl. ..................................... 433/119
(58) Field of Classification Search ............... 433/118, 433/119, 82, 84; 601/2; 606/169, 170, 171
See application file for complete search history.

(56) References Cited

U.S. PATENT DOCUMENTS

| | | |
|---|---|---|
| 3,526,219 A | 9/1970 | Balamuth |
| 3,547,110 A | 12/1970 | Balamuth |
| 3,636,947 A | 1/1972 | Balamuth |
| 3,645,255 A | 2/1972 | Robinson |
| 3,651,576 A | 3/1972 | Massa |
| 3,654,502 A * | 4/1972 | Carmona et al. ........... 433/119 |
| 3,924,335 A | 12/1975 | Balamuth et al. |
| RE28,752 E * | 3/1976 | Balamuth et al. ........... 318/116 |
| 4,176,454 A | 12/1979 | Hatter et al. |
| 4,236,889 A | 12/1980 | Wright |
| RE30,536 E | 3/1981 | Perdreaux, Jr. |
| 4,331,422 A | 5/1982 | Heyman |
| 4,370,131 A | 1/1983 | Banko |
| 4,735,200 A | 4/1988 | Westerman |
| 4,787,847 A | 11/1988 | Martin et al. |
| 4,832,683 A | 5/1989 | Idemoto et al. |
| 5,286,192 A | 2/1994 | Dixon |
| 5,531,597 A | 7/1996 | Foulkes et al. |
| 5,704,787 A | 1/1998 | Hickok et al. |
| 5,772,434 A | 6/1998 | Winston |
| 5,775,901 A | 7/1998 | Riso |
| 5,853,290 A | 12/1998 | Winston |
| 6,386,866 B1 | 5/2002 | Hecht et al. |
| 2002/0040198 A1 | 4/2002 | Rahman et al. |
| 2002/0127512 A1 | 9/2002 | Chen et al. |
| 2003/0022129 A1 | 1/2003 | Rahman et al. |
| 2003/0073055 A1 | 4/2003 | Pollock et al. |
| 2003/0108844 A1 | 6/2003 | Rahman et al. |

* cited by examiner

*Primary Examiner*—Cary E. O'Connor
(74) *Attorney, Agent, or Firm*—Christie, Parker & Hale, LLP (57) ABSTRACT

An insert for an ultrasonic dental unit is provided. The insert includes a transducer for generating ultrasonic vibrations, and a tip for applying the ultrasonic vibrations at a location inside the mouth of a patient. A connecting body is disposed between and attached to the transducer and the tip. The connecting body transmits the ultrasonic vibrations from the transducer to the tip. A retaining ring is snapped onto the connecting body. A hand grip is fitted at least partially over the connecting body and the retaining ring.

25 Claims, 6 Drawing Sheets

ULTRASONIC DENTAL INSERT HAVING A HAND GRIP FITTED TO A RETAINING RING

CROSS-REFERENCE TO RELATED APPLICATIONS

This application claims the priority to and the benefit of U.S. Provisional Patent Application No. 60/432,653 entitled "Ultrasonic Swivel Insert" filed Dec. 12, 2002 and U.S. Provisional Patent Application No. 60/524,904 entitled "Ultrasonic Inserts for Dental Hygiene Tools" filed Nov. 26, 2003, the entire contents of both of which are incorporated herein by reference.

This application contains subject matter related to the subject matter disclosed in a commonly owned U.S. patent application Ser. No. 10/735,050 entitled "Ultrasonic Dental Handpiece Having a Rotatable Head," filed Dec. 12, 2003, the entire content of which is incorporated herein by reference.

FIELD OF THE INVENTION

The present invention is related to ultrasonic dental tools, and particularly to an ultrasonic dental insert having a snap-on retaining ring and a hand grip.

BACKGROUND

Dental practitioners use ultrasonic dental tools (instruments) for dental treatments and procedures, such as scaling, periodontal treatments, root canal therapy, and the like. The ultrasonic dental tools typically include a handpiece coupled at one end (i.e., a proximal end) to an electrical energy and fluid source via a cable. The cable includes a hose to provide fluid (e.g., water) and conductors to provide electrical energy.

The other end (i.e., a distal end) of the handpiece has an opening intended to receive a replaceable insert with a transducer (e.g., magnetostrictive) carried on the insert. The transducer extends from a proximal end of the insert into a hollow interior of the handpiece. An ultrasonically vibrated tip extends from a distal end of the insert.

The insert typically includes a metal shaft, which is partially enveloped by a hand grip made of resin. The hand grip usually comes in two halves, which must be joined together with the metal shaft in between. Such use of two-piece hand grips results in a cumbersome and lengthy assembly process. Therefore, it is desirable to provide an insert and a corresponding manufacturing process that do not require such two-piece hand grip assembly.

SUMMARY

In an exemplary embodiment of the present invention, an ultrasonic dental insert includes a transducer for generating ultrasonic vibrations, and a tip for applying the ultrasonic vibrations at a location inside the mouth of a patient. A connecting body is disposed between and attached to the transducer and the tip. The connecting body transmits ultrasonic vibrations from the transducer to the tip. A retaining ring is snapped onto the connecting body. A hand grip is fitted at least partially over the connecting body and the retaining ring.

In another exemplary embodiment of the present invention, a method of assembling an ultrasonic dental insert is provided. The ultrasonic dental insert includes a tip attached to a connecting body, a transducer attached to the connecting body, a retaining ring and a hand grip. The method includes: snapping the retaining ring onto the connecting body; and fitting the hand grip to the retaining ring and the connecting body by sliding it at least partially over the connecting body and the retaining ring.

In yet another exemplary embodiment of the present invention, an ultrasonic dental unit is provided. The ultrasonic dental unit includes an insert and a handpiece. The insert includes a transducer for generating ultrasonic vibrations, and a tip for applying ultrasonic vibrations at a location inside the mouth of a patient. A connecting body is disposed between and attached to the transducer and the tip. The connecting body transmits ultrasonic vibrations from the transducer to the tip. A retaining ring is snapped onto the connecting body. A hand grip is fitted at least partially over the connecting body and the retaining ring. The handpiece receives the insert, and includes a coil assembly for energizing the transducer, and a body for housing the coil assembly and receiving the insert.

BRIEF DESCRIPTION OF THE DRAWINGS

These and other aspects of the invention may be understood by reference to the following detailed description, taken in conjunction with the accompanying drawings, wherein.

DETAILED DESCRIPTION

In exemplary embodiments of the present invention, an ultrasonic dental insert includes a retaining ring, which snaps onto a connecting body (e.g., a shaft) attached to an ultrasonic transducer. The retaining ring may be made of metal such as stainless steel, or it may be made of a suitable synthetic polymeric material, such as that commonly referred to as "plastic." Once snapped onto the connecting body, the retaining ring does not rotate. A hand grip, with an undercut on its inside, is fitted over the retaining ring and is locked into place. Such use of the retaining ring and the hand grip (e.g., a one-piece hand grip) permits assembly of the insert in less time and with less effort in comparison to using a two-piece hand grip.

Figure 1:
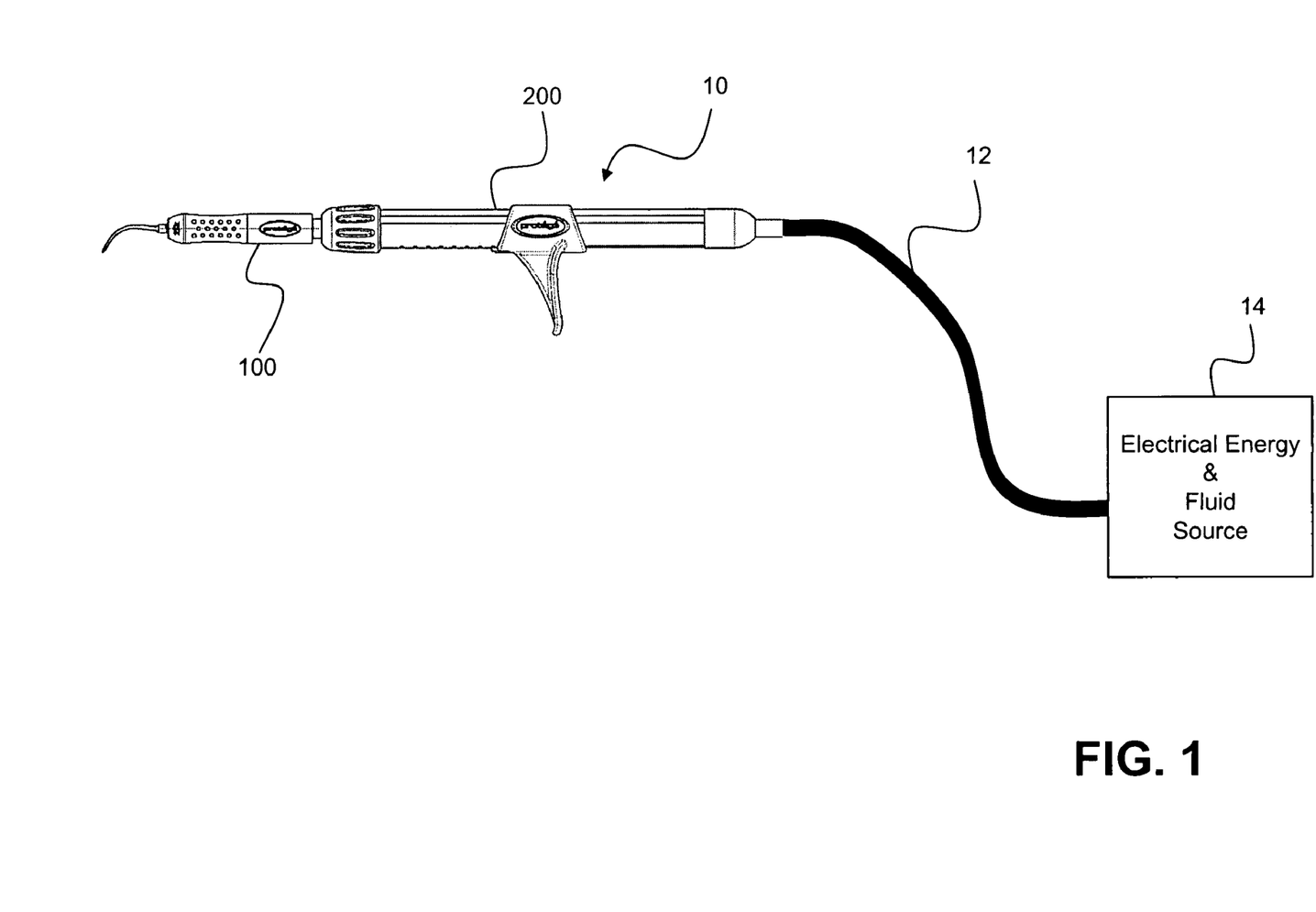
FIG. 1 illustrates an ultrasonic dental unit (or system) including an ultrasonic dental tool attached to an electrical energy & fluid source.

FIG. 1 illustrates an ultrasonic dental unit including an ultrasonic dental tool 10 attached to an electrical energy & fluid source 14 via a cable 12. The cable 12 includes a conduit for carrying fluid as well as wires for carrying electrical signals from the electrical energy & fluid source 14 to the ultrasonic dental tool 10. The ultrasonic dental tool 10 includes a handpiece 200 and an insert 100 received within the handpiece 200.

Figure 2:
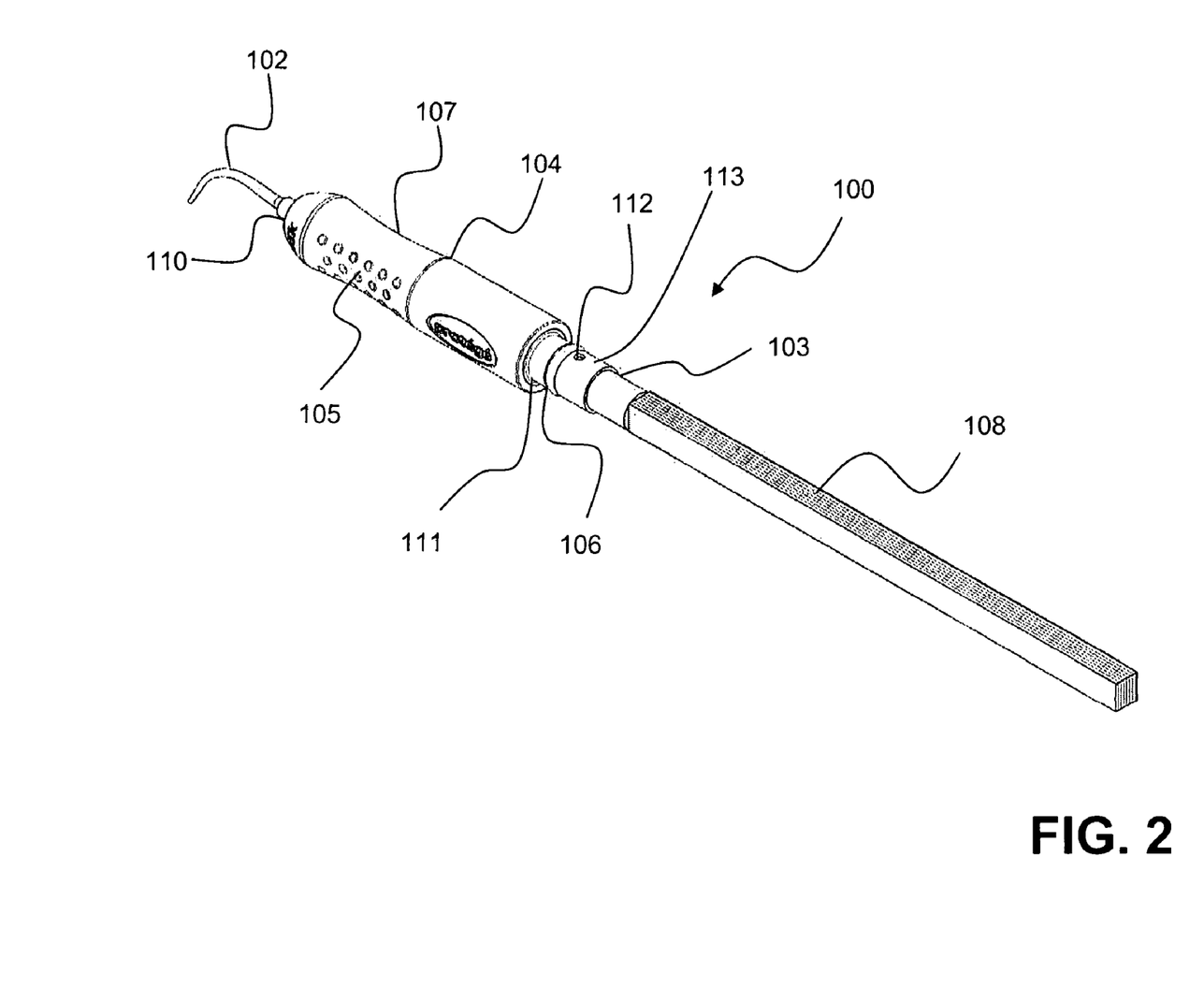
FIG. 2 is a perspective view of an ultrasonic dental insert in an exemplary embodiment of the present invention, which can be used with the ultrasonic dental unit of FIG. 1.
Figures 3, 4:
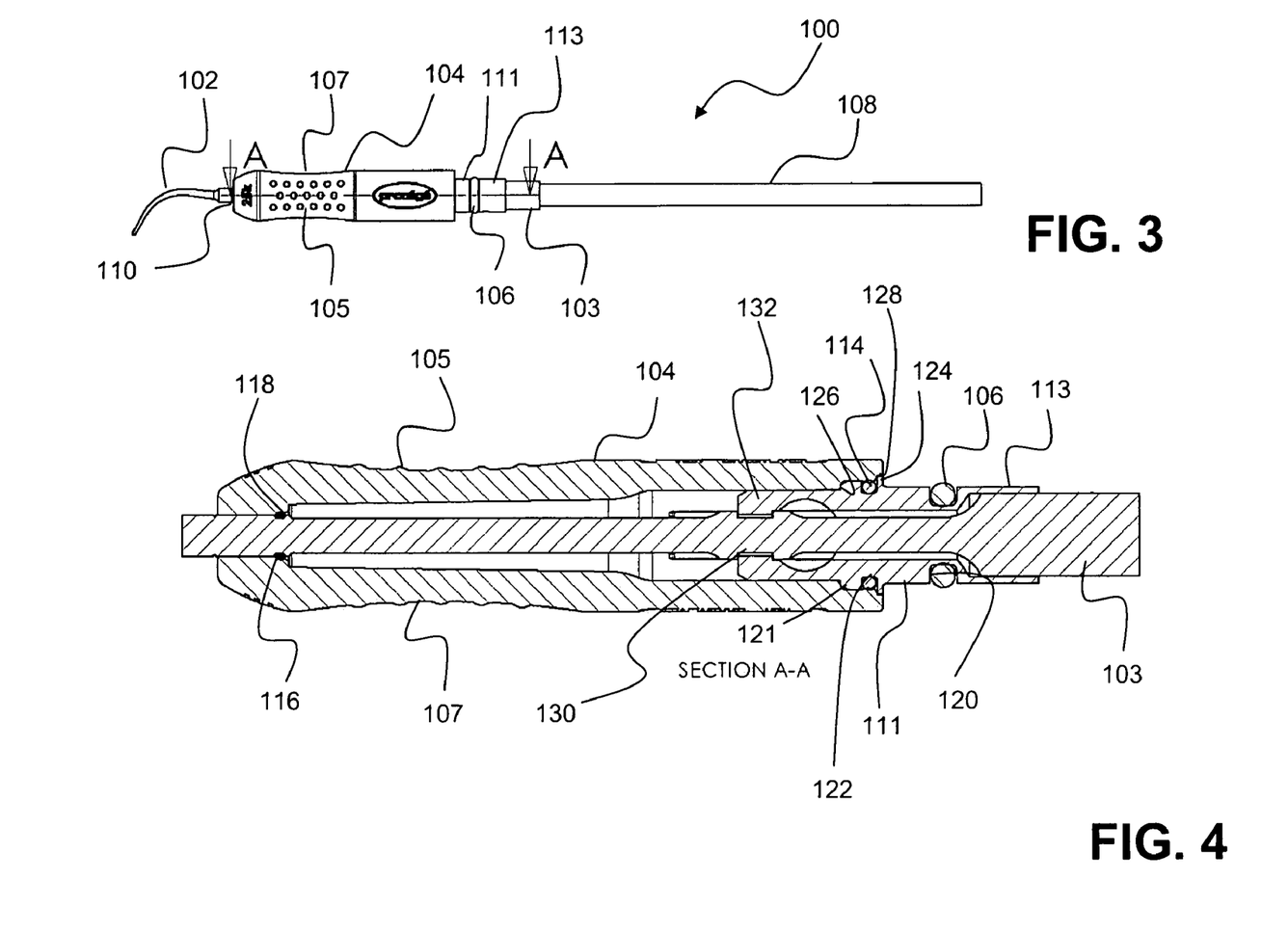
FIG. 3 is a side view of the ultrasonic dental insert of FIG. 2.
FIG. 4 is an enlarged cross-sectional view of the ultrasonic dental insert of FIG. 3 taken along the line A—A.
Figure 5:
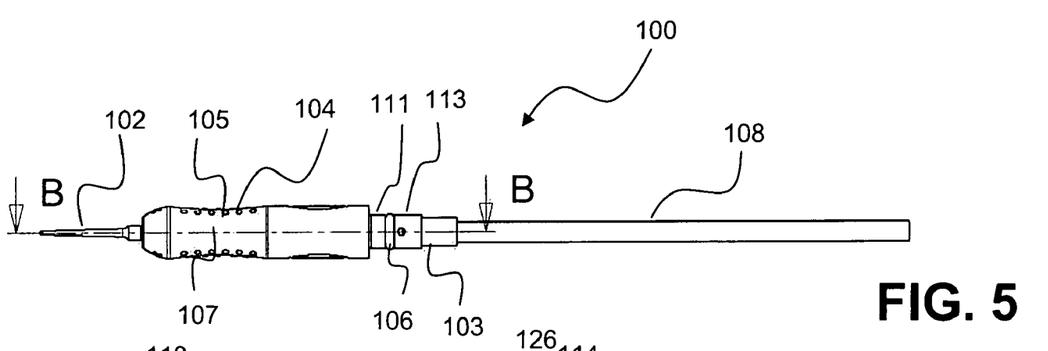
FIG. 5 is a top view of the ultrasonic dental insert of FIG. 2, which has been rotated approximately 90 degrees from the side view depicted in FIG. 3.

FIGS. 2 and 3 illustrate an ultrasonic dental insert 100 in an exemplary embodiment of the present invention. FIG. 5 is a top view of the dental insert 100, which has been rotated approximately 90 degrees from the side view depicted in FIG. 3. The dental insert 100 includes a tip 102 at its distal end and an ultrasonic transducer 108 at its proximal end. The tip 102 is coupled to the transducer 108 via a connecting body 103, which may take a form of a shaft. The connecting body is made of material suitable for transmitting ultrasonic vibrations, such as stainless steel, as it is used to deliver ultrasonic vibrations generated by the transducer 108 to the tip 102. The transducer 108, for example, may be attached to the connecting body 103 by soldering, welding, laser welding and/or any other suitable method. For example, the joint between the connecting body 103 and the transducer 108 may be a braze joint formed using a braze compound, which includes cadmium free silver solder and high temperature brazing flux.

The connecting body 103 has mounted thereon an annular retaining ring 111, which may also be made of metal such as stainless steel. The retaining ring 111 also has a connecting portion 113, which defines a generally cylindrical cavity formed therein for receiving a corresponding portion of the connecting body 103 in a force fit relationship. The retaining ring is fixedly attached (e.g., snapped on as described below in reference to FIGS. 4, 6 and 7) to the connecting body 103 such that it neither rotates nor moves laterally along the axis of the connecting body.

The ultrasonic dental insert 100 also includes a hand grip 104, which may be made of high temperature resin. For example, the hand grip 104 may be fabricated using ULTEM®, which is an amorphous thermoplastic polyetherimide available from GE Plastics. The hand grip 104 has a generally cylindrical shape, and is fitted over the retaining ring 111 and locked in place, such that the retaining ring 111 and the connecting body 103 are secured to the hand grip 104. The hand grip 104 is removably coupled to the connecting body 103 and the retaining ring 111, such that the hand grip can be separated from them.

Along its outer surface, the hand grip 104 has a contour and a slightly concave area 107, enabling it to be easily grasped by a dental practitioner. The hand grip 104 also has formed thereon a plurality of bumps 105 on its external surface to further facilitate grasping of the device by a dental practitioner. The hand grip 104 also has formed thereon (i.e., defines) a passageway 110 at its distal end near the tip 102 for delivering fluid (e.g., water) to the gum or tooth of the patient.

The retaining ring 111 has an opening 112 formed thereon for receiving fluid from the handpiece 200. The fluid may exit through the passageway 110 of the hand grip 104. In other embodiments, the insert 100 may have an opening at the end of its tip 102, a groove formed on the tip, or an external tube for enabling the fluid to exit the insert.

The transducer 108, for example, may be formed from a stack of thin nickel plates (e.g., 16 laminated nickel alloy strips, which are 90% nickel manganese (NiMn)) that are arranged in parallel. The nickel plates may be joined together at both ends at a braze joint using, for example, a braze compound including cadmium free silver solder and high temperature brazing flux. The insert 100 is a magnetostrictive type wherein the nickel plates 108 can convert the electrical energy into ultrasonic vibrations when, for example, coils in the handpiece are energized using the electrical signals from the cable. The insert 100 has an O-ring 106 mounted thereon for engaging and pressing against the inner surface of the handpiece 200 such as to form a water tight seal. For handpieces having a rotatable rotator head, the O-ring 106 may engage the rotator head such that the ultrasonic dental insert rotates together with the rotator head.

During operation, the stack of thin nickel plates 108 vibrate at a frequency equal to the stack's natural frequency with excitation induced by coils. After placing the insert in the handpiece and the electrical energy source is powered on, the operator manually tunes the frequency of the electrical energy source until it reaches the resonance frequency, i.e., the natural frequency of the insert. Alternatively, autotune units may automatically lock on the insert resonance frequency once powered on. At this time, the stack begins vibrating. This vibration of the stack is amplified and transmitted to the tip 102 through the connecting body 103. Ultrasonic inserts used in the United States are typically designed to vibrate at 25 kHz or 30 kHz frequencies.

Figure 6:
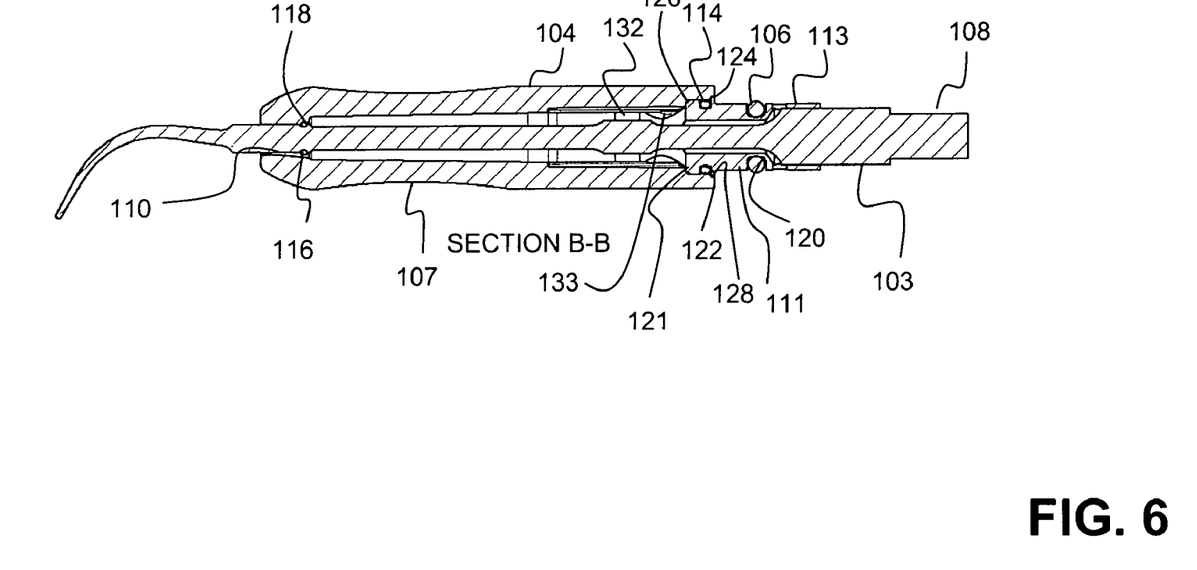
FIG. 6 is an enlarged cross-sectional view of the ultrasonic dental insert of FIG. 5 taken along the line B—B.
Figure 7:
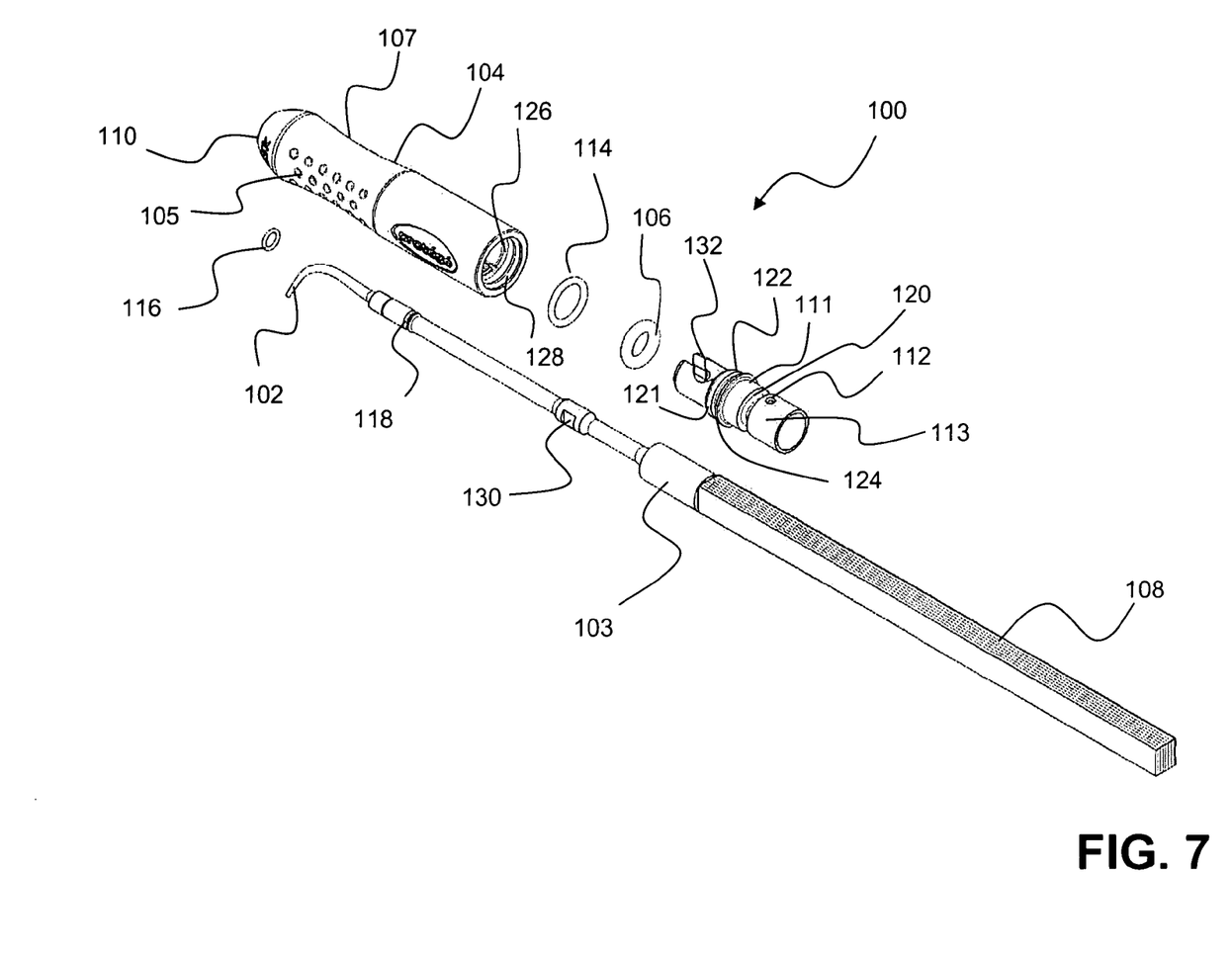
FIG. 7 is an exploded perspective view of the ultrasonic dental insert of FIG. 2.

Referring now to FIGS. 4, 6 and 7, the connecting body 103 has formed thereon a circular groove 118 near its distal end. An O-ring 116 is seated in the groove 118. When the hand grip 104 is fitted onto the connecting member 103, the O-ring 116 provides a seal between the connecting member 103 and the hand grip 104 so as to prevent undesired fluid leakage.

The retaining ring 111 has a generally cylindrical shape, and has formed thereon a connecting portion 113 fitting over a corresponding cylindrical portion of the connecting body 103. The opening 112 for receiving fluid from the handpiece is formed on the side of the connecting portion 113. The retaining ring 111 has formed thereon, adjacent to the connecting portion 113, a circular groove 120 for seating the external O-ring 106.

At the distal end, the retaining ring 111 has formed thereon a pair of gripping elements 132 that face each other. Each gripping element has an end portion that protrudes inwardly toward the end portion of the other gripping element. The connecting body 103 has a pair of indentations 130 formed thereon for receiving the protruding end portions of the gripping elements such that the gripping elements 132 are snapped into the indentations 130. Thus engaged, the retaining ring 111 of the illustrated embodiment is locked to the connecting body 103, and neither rotates nor moves laterally with respect to the same.

The hand grip 104 on its inner surface may have formed thereon an inward protrusion 133 for guiding the hand grip 104 to fit over the retaining ring 111. The protrusion 133, for example, engages a gap between the gripping elements 132 so that the hand grip 104 is not rotatable with respect to the connecting body 103, once the hand grip 104 is fitted over the connecting body 103.

The retaining ring 111 also has formed thereon circular flanges 121, 124 and a circular groove 122. The circular groove 122 is for seating the O-ring 114. The hand grip 104 has an undercut 126 formed therein for fitting over the distal end of the retaining ring 111, and engaging the flange 121. The undercut, for example, is circular in shape.

The hand grip 104 has also formed thereon a depressed region 128 below the undercut on its inner surface, which is used to engage the flange 124 and further prevent the retaining ring 111 from moving into the hand grip 104. The depressed region 128, for example, is also circular in shape, wherein the depressed region 128 has a radius larger than that of the undercut 126. The undercut 126 and the depressed region 128 fit tightly with the flanges 121 and 124, respectively.

Figure 8:
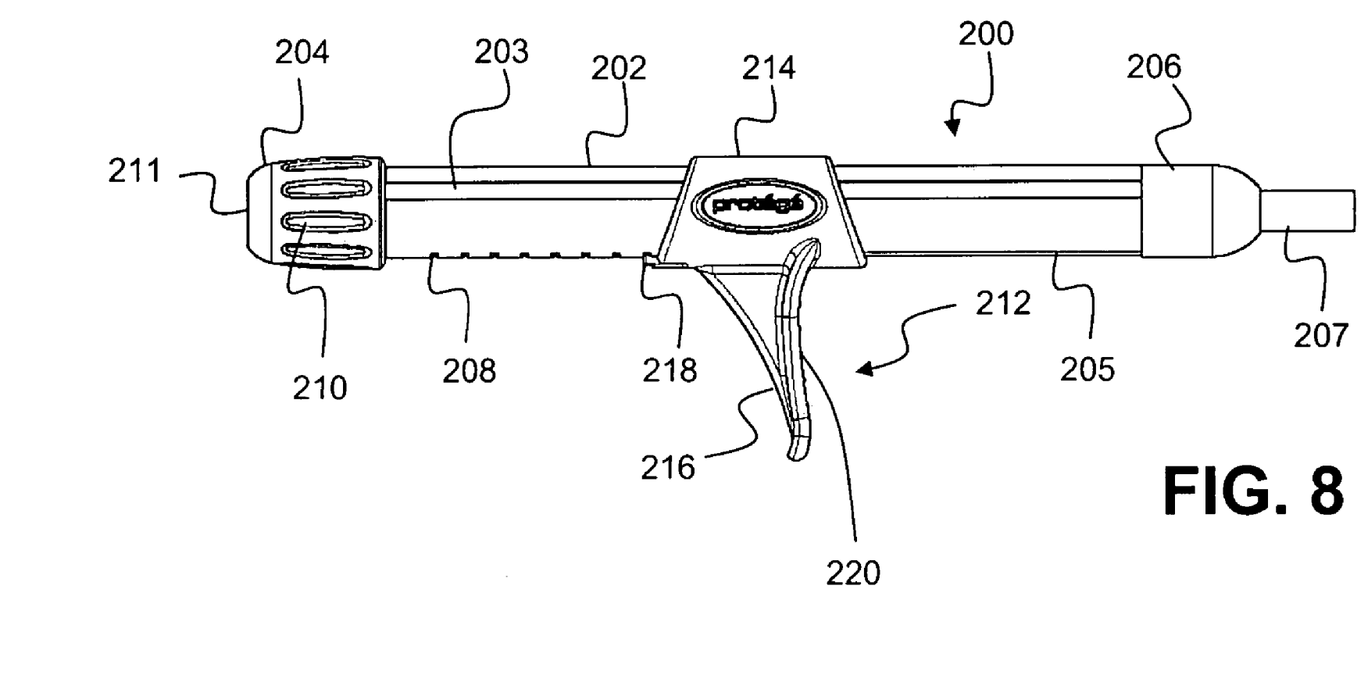
FIG. 8 is a side view of an ultrasonic dental handpiece that can be used with the ultrasonic dental insert of FIG. 2.

FIG. 8 illustrates a side view of a handpiece 200 that can receive the insert 100 as seen, for example, in FIG. 1. The handpiece 200 includes a body 202, a rotator head 204 and an interconnect 206. The rotator head 204 located at a distal end of the handpiece 200 is rotatably coupled to the rest of the handpiece 200. When the insert 100 is installed in the handpiece 200, the O-ring 106 is pressure fitted with an inner surface of the rotator head 204, such that the insert 100 rotates together with the rotator head 204.

The interconnect 206 located at a proximal end of the handpiece 200 is coupled to a cable (e.g., the cable 12 of FIG. 1) for providing electrical signals as well as fluid (e.g., water) to the handpiece 200. The interconnect 206 has a strain reliever 207 formed thereon to relieve strain between the interconnect 206 and the cable.

Since the body 202 is fixedly coupled to the interconnect 206, which in turn is fixedly attached to the cable, the handpiece 200 cannot be rotated easily. Therefore, by allowing the rotator head 204 to rotate with respect to the rest of the handpiece 200, the dental practitioner need not repeatedly re-orient the entire dental tool to treat different teeth and/or different areas of a tooth. Further, since the rotator head 204 of the handpiece 200 can be rotated rather easily with respect to the body 202, the dental practitioner need not take the insert out of the patient's mouth and rotate the insert using both hands to re-orient the tip of the insert at a desired angular position. Therefore, time associated with re-orienting the tip a number of times during the dental treatment is reduced, and the flow of work is not interrupted as much, thereby resulting in a smooth work flow and reduction of time.

The rotator head 204 has a generally cylindrical shape, a hollow interior, and an opening at each end of the interior, which is used to receive the distal end of the body 202 at one end and a dental insert at the other end. For example, at its distal end, the rotator head 204 has formed thereon an opening 211 for receiving the ultrasonic dental insert 100.

The rotator head 204 has formed around its outer peripheral surface a plurality of indentations 210. Each indentation 210 has an elongated elliptical (or rectangular) shape with its major axis in the direction parallel to the central axis of the handpiece 200. The indentations 210 facilitate grasping of the rotator head 204 by a dental practitioner to rotate, for example, it with respect to the body 202 (e.g., using only one hand). In other embodiments, the rotator head 204 may have a number of protrusions formed thereon instead of the indentations.

The body 202 has formed thereon a pair of grooves 203 that are equidistant from the top and traverse substantially the whole length of the body 202. The grooves 203 are used to mount a hand grip 212 on the handpiece 200. The body 202 has also formed thereon at its bottom near the distal end of the body 202 a plurality of substantially evenly spaced slots 208 that are used to keep the hand grip 212 from moving in the direction of the axis of the handpiece 200. The body 202 has also formed thereon at its bottom near the proximal end a groove 205 that is co-linear to the slots 208. The groove 205 engages the hand grip 212 together with the grooves 203 to keep the hand grip 212 from rotating about the central axis of the handpiece 200. The grooves may not be used in other embodiments.

The hand grip 212 has an engagement portion 214, which has a generally cylindrical shape and a hollow interior. The engagement portion 214 is slipped onto the body 202 similar to a sleeve, and engages the body 202 such that the engagement portion envelopes a portion of the body 202. The engagement portion has formed thereon a resilient cantilever portion 218, which is used to engage one of the slots 208 on the body 202. The engagement portion 214 has attached to its bottom surface a handle 216, which is used by a dental practitioner to hold the handpiece 200 during dental procedures. The handle also facilitates rotating of the rotator head 204 using one hand. The handle 216 has formed on its back surface a plurality of indentations or protrusions 220, which are used to facilitate grasping by a dental practitioner.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

We claim:

1. An ultrasonic dental insert comprising:
   a transducer for generating ultrasonic vibrations;
   a tip for applying the ultrasonic vibrations at a location inside the mouth of a patient;
   a connecting body disposed between and attached to the transducer and the tip, the connecting body for transmitting the ultrasonic vibrations from the transducer to the tip;
   a retaining ring snapped onto the connecting body, the retaining ring having a hole on its periphery; and
   a hand grip fitted at least partially over the connecting body and the retaining ring.

2. The ultrasonic dental insert of claim 1, wherein the retaining ring has a connecting portion for fitting over a corresponding portion of the connecting body, wherein the hole is formed on a surface of the connecting portion.

3. The ultrasonic dental insert of claim 1, wherein the hand grip defines a passageway formed near the tip for delivering fluid to the location inside the mouth.

4. The ultrasonic dental insert of claim 1, further comprising a first O-ring, wherein the retaining ring has a first groove formed thereon for seating the first O-ring, and wherein the first O-ring provides a water tight sealing between the retaining ring and the hand grip.

5. The ultrasonic dental insert of claim 4, further comprising a second O-ring, wherein the retaining ring has a second groove formed thereon for seating the second O-ring, and wherein the second O-ring provides a pressure fitting engagement between the ultrasonic dental insert and an ultrasonic dental handpiece.

6. The ultrasonic dental insert of claim 1, wherein the hand grip has an undercut formed on its inside surface, wherein the retaining ring has a first flange formed thereon, and wherein the first flange fits tightly with the undercut.

7. The ultrasonic dental insert of claim 6, wherein the hand grip has a depressed region formed on its inside surface below the undercut, wherein a radius of the depressed region is larger than that of the undercut, wherein the retaining ring has a second flange formed thereon, and wherein the second flange fits tightly with the depressed region.

8. The ultrasonic dental insert of claim 1, further comprising an O-ring, wherein the connecting body has a groove formed thereon for seating the O-ring, and wherein the O-ring forms a seal with an opening of the hand grip near the tip, so as to prevent undesired water leakage.

9. The ultrasonic dental insert of claim 1, wherein the transducer comprises a stack of nickel plates.

10. The ultrasonic dental insert of claim 1, wherein the hand grip has a protrusion formed on its inner surface for guiding the hand grip to fit over the retaining ring.

11. The ultrasonic dental insert of claim 10, wherein the retaining ring comprises a hole on its surface adapted for passing fluid into the ultrasonic dental insert.

12. An ultrasonic dental insert comprising:
a transducer for generating ultrasonic vibrations;
a tip for applying the ultrasonic vibrations at a location inside the mouth of a patient;
a connecting body disposed between and attached to the transducer and the tip, the connecting body for transmitting the ultrasonic vibrations from the transducer to the tip;
a retaining ring snapped onto the connecting body; and
a hand grip fitted at least partially over the connecting body and the retaining ring,
wherein the retaining ring comprises a pair of gripping elements for snapping onto the connecting body.

13. The ultrasonic dental insert of claim 12, wherein the connecting body has formed thereon a pair of indentations for engaging the pair of gripping elements.

14. A method of assembling an ultrasonic dental insert comprising a tip attached to a connecting body, a transducer attached to the connecting body, a retaining ring and a hand grip, the method comprising:
snapping the retaining ring onto the connecting body, the retaining ring having a hole formed on its surface, adapted for passing fluid into the ultrasonic dental insert; and
fitting the hand grip to the retaining ring and the connecting body by sliding it at least partially over the connecting body and the retaining ring.

15. The method of claim 14, wherein the retaining ring includes a pair of gripping elements, and wherein the snapping comprises snapping the pair of gripping elements onto the connecting body.

16. The method of claim 15, wherein the connecting body has formed thereon a pair of indentations, and wherein the snapping comprises snapping the pair of gripping elements into the pair of indentations.

17. The method of claim 14, wherein the retaining, ring includes a connecting portion, and snapping comprises fitting the connecting portion over a corresponding portion of the connecting body.

18. An ultrasonic dental unit comprising:
an insert comprising:
a transducer for generating ultrasonic vibrations;
a tip for applying the ultrasonic vibrations at a location inside the mouth of a patient;
a connecting body disposed between and attached to the transducer and the tip, the connecting body for transmitting the ultrasonic vibrations from the transducer to the tip;
a retaining ring snapped onto the connecting body; and
a hand grip fitted at least partially over the connecting body and the retaining ring;
a handpiece for receiving the insert, the handpiece comprising a coil assembly for energizing the transducer, and a body for housing the coil assembly and receiving the insert.

19. The ultrasonic dental unit of claim 18, further comprising an electrical energy & fluid source for supplying electrical signals and fluid to the handpiece.

20. The ultrasonic dental unit of claim 18, wherein the retaining ring comprises a pair of gripping elements for snapping onto the connecting body.

21. The ultrasonic dental unit of claim 20, wherein the connecting body has formed thereon a pair of indentations for engaging the pair of gripping elements.

22. The ultrasonic dental unit of claim 18, wherein the retaining ring has a connecting portion for fitting over a corresponding portion of the connecting body.

23. The ultrasonic dental unit of claim 18, wherein the hand grip is slid over the connecting body in a direction of an axis of the connecting body to be fitted at least partially over the connecting body and the retaining ring.

24. An ultrasonic dental insert comprising:
a transducer for generating ultrasonic vibrations;
a tip for applying the ultrasonic vibrations at a location inside the mouth of a patient;
a connecting body disposed between and attached to the transducer and the tip, the connecting body for transmitting the ultrasonic vibrations from the transducer to the tip;
a retaining ring snapped onto the connecting body, the retaining ring having a hole formed on its surface, adapted for passing fluid into the ultrasonic dental insert; and
a hand grip fitted at least partially over the connecting body and the retaining ring.

25. The ultrasonic dental insert of claim 24, wherein the hand grip has a protrusion formed on its inner surface for guiding the hand grip to fit over the retaining ring.

* * * * *

UNITED STATES PATENT AND TRADEMARK OFFICE
CERTIFICATE OF CORRECTION

PATENT NO.        : 7,044,736 B2                                            Page 1 of 1
APPLICATION NO.   : 10/734517
DATED             : May 16, 2006
INVENTOR(S)       : Atkin et al.

It is certified that error appears in the above-identified patent and that said Letters Patent is hereby corrected as shown below:

On the Title Page

| | |
|---|---|
| (60) Related U.S. Application Data | Delete "Provisional application No. 60/432,653, filed on December 12, 2002", Insert -- Provisional application Nos. 60/432,653, filed on December 12, 2002 and 60/524,904, filed on November 26, 2003-- |
| Column 7, line 42, Claim 17 | Delete "retaining,", Insert --retaining-- |
| Column 8, line 15, Claim 19 | Delete "&", Insert --and-- |

Signed and Sealed this

Ninth Day of January, 2007

JON W. DUDAS
*Director of the United States Patent and Trademark Office*